United States Patent
Lacoste et al.

(10) Patent No.: US 11,120,257 B2
(45) Date of Patent: Sep. 14, 2021

(54) RATIONALIZING NETWORK PREDICTIONS USING SIMILARITY TO KNOWN CONNECTIONS

(71) Applicant: INTERNATIONAL BUSINESS MACHINES CORPORATION, Armonk, NY (US)

(72) Inventors: Alix Lacoste, Brooklyn, NY (US); William S. Spangler, San Jose, CA (US); Feng Wang, Santa Clara, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 14 days.

(21) Appl. No.: 16/799,530

(22) Filed: Feb. 24, 2020

(65) Prior Publication Data
US 2020/0193154 A1  Jun. 18, 2020

Related U.S. Application Data

(63) Continuation of application No. 15/821,063, filed on Nov. 22, 2017, now Pat. No. 10,607,074.

(51) Int. Cl.
  *G06K 9/00* (2006.01)
  *G06N 7/00* (2006.01)
  (Continued)

(52) U.S. Cl.
  CPC ......... *G06K 9/00476* (2013.01); *G06F 17/17* (2013.01); *G06K 9/00147* (2013.01);
  (Continued)

(58) Field of Classification Search
  CPC ... G06K 9/00463–00476; G06K 9/623; G06K 9/4638; G06K 9/00147;
  (Continued)

(56) References Cited

U.S. PATENT DOCUMENTS 8,255,975 B2  8/2012  Li et al.
9,336,311 B1  5/2016  Amarillo et al.
(Continued)

OTHER PUBLICATIONS

Tao et al., "Information theory applied to the sparse gene ontology annotation network to predict novel gene function," Bioinformatics, 23(13): i529-i538 (2007).

*Primary Examiner* — Michael S Osinski
(74) *Attorney, Agent, or Firm* — Erik Huestis; Stephen Kenny; Foley Hoag LLP

(57) ABSTRACT

Rationalization of network predictions using similarity to known connections is provided. In various embodiments, a graph is read. The graph comprises a plurality of nodes. Each of the plurality of nodes corresponds to an entity or property. The plurality of nodes is interconnected by a plurality of edges. Each edge corresponds to a relationship between connected nodes. A new edge in the graph is predicted. The new edge corresponds to a relationship between a first node and a second node. The first node corresponds to an entity and the second node corresponds to an entity or property. One or more additional nodes connected to the second node is located. The one or more additional nodes is scored according to its connections in common with the first node. One or more sources is provided to a user describing the connection between the one or more additional node and the second node.

15 Claims, 4 Drawing Sheets

(51) Int. Cl.
  *G06K 9/62* (2006.01)
  *G06K 9/46* (2006.01)
  *G06F 17/17* (2006.01)
(52) U.S. Cl.
  CPC ........... *G06K 9/4638* (2013.01); *G06K 9/623* (2013.01); *G06K 9/6224* (2013.01); *G06K 9/6269* (2013.01); *G06N 7/005* (2013.01)
(58) Field of Classification Search
  CPC .... G06K 9/6224; G06K 9/6269; G06N 7/005; G06N 5/022; G06F 17/17; G06F 17/2705; G06F 17/30979; G06F 17/30864; G06F 17/3053; G06F 17/30867; G06F 17/30539; G06F 17/30011; G06F 17/3089; G06F 17/3087; G06F 17/30424; G06F 17/30657; G06F 17/30663; G06F 17/30873; G06F 17/30893; G06F 16/9024; G06F 16/24578; G06F 16/248; G06F 16/288; G06T 11/206; G16B 40/00
  See application file for complete search history.

(56) References Cited

U.S. PATENT DOCUMENTS

| | | | |
|---|---|---|---|
| 9,881,077 B1 | 1/2018 | Alfonseca et al. | |
| 10,180,969 B2 | 1/2019 | Trudel et al. | |
| 10,380,703 B2 | 8/2019 | Chrapko et al. | |
| 2009/0106184 A1 | 4/2009 | Lang et al. | |
| 2009/0313463 A1 | 12/2009 | Pang et al. | |
| 2010/0179874 A1 | 7/2010 | Higgins et al. | |
| 2011/0078205 A1 | 3/2011 | Salkeld et al. | |
| 2013/0144899 A1 | 6/2013 | Lee et al. | |
| 2013/0151543 A1 | 6/2013 | Fan et al. | |
| 2014/0279306 A1* | 9/2014 | Shi | G06Q 40/12 705/30 |
| 2015/0033106 A1 | 1/2015 | Stetson et al. | |
| 2015/0095348 A1 | 4/2015 | Presta et al. | |
| 2015/0249669 A1 | 9/2015 | Gamage et al. | |
| 2015/0264063 A1* | 9/2015 | Jenson | G06Q 20/384 726/22 |
| 2015/0379405 A1* | 12/2015 | Jenson | G06F 21/552 706/47 |
| 2016/0154895 A1* | 6/2016 | Koutra | G06N 5/048 706/46 |
| 2017/0221240 A1 | 8/2017 | Stetson et al. | |
| 2017/0255621 A1 | 9/2017 | Kenthapadi et al. | |
| 2017/0337260 A1 | 11/2017 | Wang et al. | |
| 2018/0004822 A1 | 1/2018 | Mulder et al. | |
| 2018/0024989 A1 | 1/2018 | Bharti et al. | |
| 2018/0316722 A1 | 11/2018 | Jenson | |
| 2018/0349371 A1 | 12/2018 | Bessiere et al. | |
| 2019/0005071 A1 | 1/2019 | Kvalnes et al. | |
| 2019/0005072 A1 | 1/2019 | Kvalnes et al. | |
| 2019/0213254 A1 | 7/2019 | Ray et al. | |
| 2019/0220503 A1 | 7/2019 | Gelosi | |

* cited by examiner

RATIONALIZING NETWORK PREDICTIONS USING SIMILARITY TO KNOWN CONNECTIONS

CROSS-REFERENCE TO RELATED APPLICATIONS

This application is a continuation of U.S. application Ser. No. 15/821,063, filed Nov. 22, 2017, which is hereby incorporated by reference in its entirety.

BACKGROUND

Embodiments of the present disclosure relate to providing context for predicted biologic connections, and more specifically, to rationalizing network predictions using similarity to known connections.

BRIEF SUMMARY

According to embodiments of the present disclosure, methods of and computer program products for providing context for predicted biologic connections are provided. In various embodiments, a graph is read. The graph comprises a plurality of nodes. Each of the plurality of nodes corresponds to an entity or property. The plurality of nodes is interconnected by a plurality of edges. Each edge corresponds to a relationship between connected nodes. A new edge in the graph is predicted. The new edge corresponds to a relationship between a first node and a second node. The first node corresponds to an entity and the second node corresponds to an entity or property. One or more additional nodes connected to the second node is located. The one or more additional nodes is scored according to its connections in common with the first node. One or more sources is provided to a user describing the connection between the one or more additional node and the second node.

DETAILED DESCRIPTION

Figure 1:
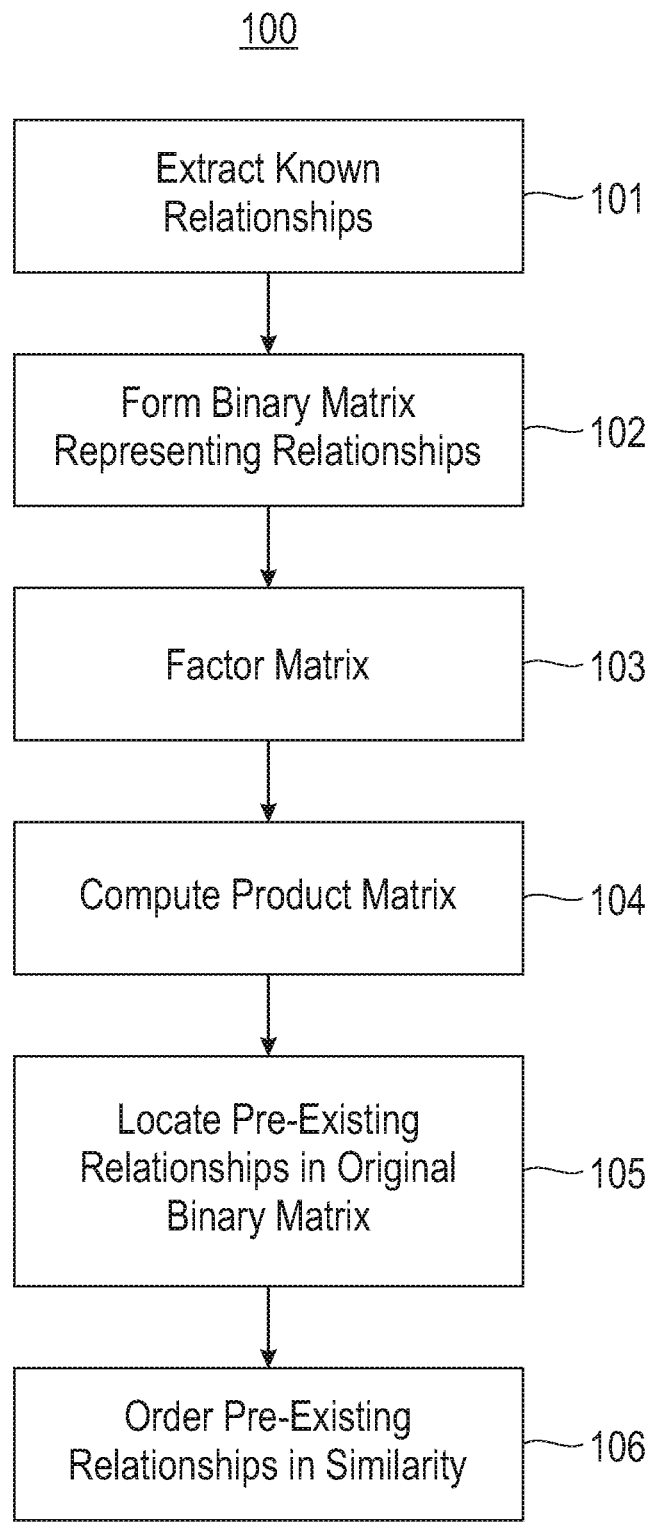
FIG. 1 illustrates a method of evaluating the consistency of relationships of biologic entities according to embodiments of the present disclosure.

In order to define concepts for discovery in a given domain, it is first necessary to define a domain specific ontology of entities and relationships that represent the state of knowledge in that domain. The entities represent objects in the physical world whose type can be identified by their structure. Example of such entities include a species, a chemical, or a gene. Each of these entities has a canonical form that is recognized scientifically as uniquely referring to that individual type, regardless of other ways that type might be expressed in scientific literature.

It is also necessary to identify certain qualitative properties or relationships that each entity may possess. These can be experimental, phenotypic properties, such as relationships between gene and trait, or relationships that are observed to take place in dynamic processes, such as one protein of a certain type interacting with another protein of a different type in a cellular process. These entity-entity or entity-property connections correspond to qualitative findings in science. They are typically found through experimentation and measurement in the lab or the field, and require independent verification to be considered established fact.

Beyond qualitative findings there are predictions and hypotheses, these may represent connections that are not yet known to exist, but hypothetically could exist, and might be validated through a proposed experiment. Computers may use the connections that exist to predict likely new connections using algorithms such as matrix factorization.

Computer models can make predictions or generate a hypothesis that synthesizes facts known about the state of the world to deduce facts that are likely based on the implications of those facts. Unfortunately, such models often utilize thousands of variables, making it difficult to explain the rationale behind such a prediction in terms that an end user of the computer model can understand.

Accordingly, there remains a need to tie the prediction back to a few known key facts that provide a convincing explanation for the prediction to help the user judge its validity. As set forth in further detail below, the present disclosure enables explaining these predictions in terms that a scientist can understand, so that the scientist may better know whether to trust this result.

In various embodiments, an automated approach is provided for explaining a given computer prediction by identifying an analogous fact or facts that are very similar to the prediction. To do this, a set of known scientific relationships is represented as a matrix, X, of zeros and ones, with one indicating the presence of a relationship and zero indicating its absence. The matrix is factored into $X \approx H \cdot W$ (H, W being two dense matrices). The relative strength of a predicted relationship is then related to the size of that relationship's value in the product matrix. A rationale may be provided for this value by finding similar rows or columns in the original matrix that contain a 1 in the corresponding position of the prediction. The evidence for these known connections then becomes indirect evidence for the predicted connection.

In various embodiments, text analysis is used to discover entity-entity relationships and entity properties by extracting from published literature, sentences of the form A (an agent) acts-on B (a target), or A (an agent) has-property B (a target). The connection between A and B is inferred from the fact that A is a subject and B is the object of the sentence and the type of relationship between A and B is inferred from the verb. A domain specific ontology of entities and interactions helps to correctly identify the end points and the type of each relationship that is thus extracted from the raw text. The result is a graph of connected nodes, where each node is an entity or property of a known type, and each link is a relationship of a known type.

This graph can now be represented as a binary matrix, X, having M rows and N columns, where each row represents a unique agent and each column represents a unique target. Then $X[m, n]==0$ iff there is no existing relationship between agent m and target n. $X[m, n]==1$ iff there exists at least one relationship where m is the agent and n is the target.

In most scientific endeavors, the number of possible agent/target relationships in the universe of possible agents and targets is quite large compared to what is actually observed to occur. Therefore the matrix X will be sparse (mostly zero). Such a matrix is a good candidate for factorization, a process that approximates a sparse matrix by two dense matrices (H,W) which are multiplied together to yield something that is approximately the same as X. The reason such an approximation may be desirable in practice is that the relationships themselves are extracted imperfectly and incompletely from data, which is itself imperfect. Therefore, X itself is a matrix which likely has some incorrect or missing values.

The product matrix therefore is not simply an approximation of X, but in some cases leads to predicted values, which are meaningful where inconsistent with X, or as a confidence measure. For the scientist to understand and act upon this signal, it is necessary to provide some kind of evidence. As set out herein, such evidence may be provided in the form of analogous entities that are as similar as possible to the entities connected hypothetically, but also already contain the connection that is being predicted. The direct evidence for these connections then becomes indirect evidence for the predicted connection.

Alternative approaches may focus on individual features, listed in order of significance. However, the feature lists in and of themselves do not correspond to individual scientific facts. They are just overall qualities of entities. This leaves the scientist unable to resolve the provenance of those overall feature weightings. In contrast, the approaches described herein require no special data science training on the part of the user to interpret their significance.

With reference now to FIG. 1, a method for evaluating the consistency of relationships of biologic entities is illustrated according to embodiments of the present disclosure. The process of evaluating the consistency of a relationship between entities, or between entities and a property, starts at 101 with extracting the known relationships from publications. At 102, these relationships are then represented as a binary matrix. The score in this matrix for the relationship to be evaluated is set to zero. At 103, this matrix is then factored into H·W. At 104, a the product matrix of H·W is computed. The score of the relationship is its value in the product matrix of H·W. The explanation for a high predicted value for any particular relationship can then be found at 105 by finding all the columns or rows in the original binary matrix that have a 1 in that cell. At 106, these pre-existing relationships are then ordered by similarity to the original row and column of the prediction. In some embodiments, similarity is calculated by looking at the number of shared features and considering the frequency of the features to determine the relative likelihood of seeing that many features in common.

Figure 2:
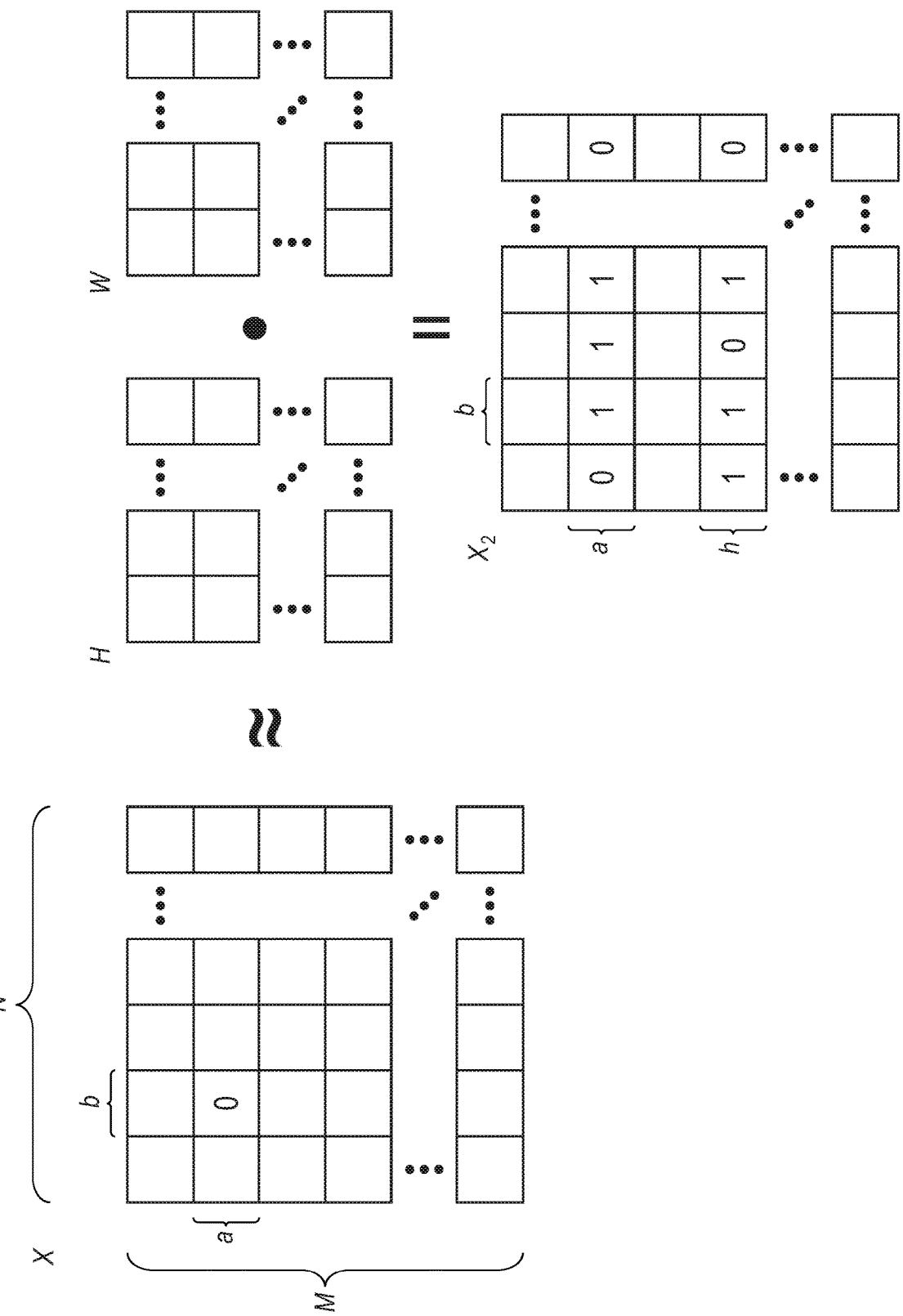
FIG. 2 illustrates exemplary entity relationship matrices according to embodiments of the present disclosure.

The above-summarized method is described in further detail below with reference to the schematic matrices depicted in FIG. 2.

Given a set of agents M and a set of Targets or Properties N, and directional relationships extracted from publications of the form m→n, where m∈M and n∈N, the relative consistency of any particular m, n pair is calculated as follows.

A binary matrix, X, having dimension M×N is constructed containing a 1 in row m, column n iff m→n exists in the scientific literature. In various embodiments, the relationship is determined through data mining of existing literature.

Although various examples herein are described in terms of binary matrices, some embodiments include continuous value matrices. In such embodiments, values greater than one may be included to indicate higher consistency in the specific relation.

X[a, b] is set to 0 for the relationship a→b whose consistency is under evaluation. A factorization of X is computed. In some embodiments, a loss function is defined as in Equation 1 giving the loss at (i, j) assuming the input is non-negative.

$$L_{ij}(W_i^*, H_{*j}^*)$$ Equation 1

The best model is found as in Equation 2.

$$\min_{W,H} \sum_{(i,j) \in Z} L_{ij}(W_{i^*}, H_{*j})$$ Equation 2

In some embodiments, Alternating Least Squares Matrix Factorization (ALS) is used for implementation of matrix factorization, for example as provided in Apache Spark. In an exemplary embodiment leveraging Apache Spark the algorithm is configures as follows: numBlocks, the number of blocks used to parallelize computation, is set to −1 to auto-configure; rank, the number of latent factors in the model is set to 10; iterations is set to 10; lambda, which specifies the regularization parameter in ALS, is set to 0.1; implicitPrefs, which specifies whether to use the explicit feedback ALS variant or one adapted for implicit feedback data, is set to implicit; alpha, a parameter applicable to the implicit feedback variant of ALS that governs the baseline consistency in preference observations, is set to 0.1.

The resulting H, W matrices can be multiplied to produce a new matrix $X_2$. The value of $X_2[a, b]$ is the relative predictive score for the relationship a→b. To calculate the explanation for a→b, all rows besides a that have 1 in column b are located. This set is denoted H.

For each row h∈H, the count of is that are in the same column as a 1 in row a is determined. This value is denoted r. The total number of is in h is computed. This value is denoted R. The total number of columns is denoted N. The total number of is in row a is denotes n. Referring to the exemplary matrix $X_2$ of FIG. 2, r=2 because there are two columns having a 1 in both row a and row h. In this example, R=3 and n=3.

The probability $p_h$ of (N, n, R, r) is computed for each h∈H. It will be appreciated that a variety of methods are available to determine this probability, including Fisher's exact test or a Chi Square probability calculation.

The rows h∈H are sorted by probability $p_h$. The lowest probability entities are presented to a user as an explanation of why the predicted connection from a→b is likely.

Evidence for each row h ∈ H may be provided by accessing the original document from which a connection h→b was inferred. In various embodiments, the original document or excerpts thereof may be presented to the user upon selection of given predicted connection.

Alternatively, the explanation for a→b may be computed as follows. All columns besides b that have a 1 one column a are located. This set is denoted H. For each column h∈H, the count of is that are in the same row as a 1 in column b is determined. This value is denoted c. The total number of is in column h is computed. This value is denoted C. The total number of rows is denoted M. The total number of is in b is denoted m. The probability $p_h$ of (M, m, C, c) is computed for each h∈H. It will be appreciated that a variety of methods are available to determine this probability, including Fisher's exact test or a Chi Square probability calculation.

The columns $h \in H$ are sorted by probability $p_h$. The lowest probability entities are presented to a user as an explanation of why the predicted connection from a→b is likely.

Evidence for each column $h \in H$ may be provided by accessing the original document from which a connection a→h was inferred. In various embodiments, the original document or excerpts thereof may be presented to the user upon selection of given predicted connection.

Referring to Table 1-Table 2 below, an example related to bladder cancer is illustrated. In this example, evidence for top ranked gene CD4 is provided. The entities (e.g., pathways, tumor, or condition) in the rows of Table 1 and Table 2 are connected to the target CD4. Common genes indicates how many targets the entity shares with the targets in the known set of 70 genes connected to bladder cancer. Total genes indicates how many genes the entity is connected to in total. Probability indicates the p-value of sharing that many common genes by chance (e.g., determined by the chi-squared test).

TABLE 1

| Pathway | Common genes | Total genes | Probability |
| --- | --- | --- | --- |
| Immune response | 23 | 383 | 1.64E−78 |
| T cell costimulation | 6 | 80 | 5.46E−27 |
| Positive regulation of interleukin-2 biosynthetic process | 2 | 12 | 2.19E−21 |
| Cell surface receptor signaling pathway | 10 | 269 | 1.08E−20 |
| Signal transduction | 18 | 1071 | 6.78E−14 |
| Positive regulation of calcium mediated signaling | 2 | 19 | 9.22E−44 |
| Response to vitamin D | 2 | 19 | 9.22E−14 |
| T cell receptor signaling pathway | 6 | 153 | 1.01E−13 |
| Transmembrane receptor protein tyrosine kinase signaling pathway | 4 | 88 | 3.64E−11 |
| Positive regulation of peptidyl-tyrosine phosphorylation | 3 | 84 | 6.97E−07 |
| Cell adhesion | 7 | 457 | 1.92E−05 |
| Adaptive immune response | 4 | 191 | 4.98E−05 |

TABLE 2

| Tumor or Condition | Common genes | Total genes | Probability |
| --- | --- | --- | --- |
| ENCEPHALOMYELITIS, AUTOIMMUNE EXPERIMENTAL | 30 | 523 | 1.77E−97 |
| FLU, HUMAN | 22 | 329 | 2.56E−84 |
| INFLAMMATORY RESPONSE | 39 | 1039 | 9.97E−80 |
| DISSEMINATED SCLEROSIS | 30 | 658 | 8.06E−75 |
| B CELL CHRONIC LYMPHOCYTIC LEUKEMIA | 40 | 1184 | 1.24E−72 |
| RHEUMATOID ARTHRITIS | 36 | 971 | 2.05E−72 |
| EXPERIMENTAL LUNG INFLAMMATIONS | 25 | 490 | 1.83E−71 |
| AUTOIMMUNE DISEASE | 24 | 463 | 8.22E−70 |
| DISEASE, GRAFT-VERSUS-HOST | 15 | 189 | 2.74E−69 |
| BENIGN MONOCLONAL GANMMAPATHIES | 43 | 1430 | 1.65E−68 |
| ACUTE T-CELL LEUKEMIA | 22 | 411 | 2.62E−66 |
| DISEASE, VIRAL | 27 | 613 | 1.24E−65 |
| ANGIOCENTRIC LYMPHOMA | 56 | 2585 | 7.58E−67 |
| ACUTE MYELOBLASTIC LEUKEMIA | 32 | 915 | 4.33E−60 |
| ACUTE LYMPHOBLASTIC LEUKEMIA | 33 | 970 | 4.47E−60 |

In this example an explanation is provided for the predicted connection between the gene CD4 and bladder cancer. In this case the total number of genes being ranked is N=19687. The number of genes connected to bladder cancer in the knowledge network is n=70. The matrix for prediction is made up of genes on one side and pathways/conditions/tumors on the other. For the most similar pathway, "immune response", the total number of genes is 383 and the number shared with bladder cancer is 23. This gives a chi-squared probability of ChiSquared (19687, 70, 383, 23)=1.64×10$^{-78}$. And in fact, the immune response pathway is a very important pathway involved with this disease, so the result makes sense biologically.

Referring to Table 3-Table 5 below, an example related to IL6R is illustrated. An explanation for highly ranked adverse event (AE) Neutropenia is provided. The entities (e.g., genes, cell types, and drugs) in the rows are connected to the AE Neutropenia. Common AEs lists how many AEs the entity shares with the AEs in the training set. Total AEs lists how many AEs the entity is connected to in total. Probability lists the p-value of sharing that many common AEs by chance (e.g., determined by the chi-squared test).

TABLE 3

| Gene | Common AEs | To AEs | Probability |
| --- | --- | --- | --- |
| FCN1 | 3 | 13 | 5.04E−138 |
| CASC3 | 2 | 13 | 4.09E−62 |
| FCGR3B | 3 | 33 | 7.56E−55 |
| FHL3 | 1 | 4 | 4.97E−51 |
| FPR1 | 4 | 80 | 4.07E−40 |

TABLE 4

| Cell type | Common AEs | Total AEs | Probability |
| --- | --- | --- | --- |
| CD4 CELL | 7 | 138 | 2.57E−70 |
| PHAGOCYTES CELL | 3 | 32 | 1.54E−56 |
| MACROPHAGE CELL | 7 | 180 | 7.11E−54 |
| T HELPER1 CELL | 5 | 93 | 1.50E−53 |
| MYELOID CELL | 4 | 60 | 2.31E−53 |
| T HELPER2 CELL | 4 | 82 | 3.80E−39 |
| HEMATOPOIETIC CELL | 3 | 43 | 6.51E−38 |
| B CELL | 5 | 132 | 9.10E−38 |
| T CELL | 6 | 204 | 5.34E−35 |

TABLE 5

| Drug | Common AEs | Total AEs | Probability |
| --- | --- | --- | --- |
| ANDROSTENEDIOL | 2 | 7 | 2.10E−114 |
| ALDOXORUBICIN | 1 | 2 | 1.28E−100 |
| LINCOMYCIN | 2 | 8 | 3.00E−100 |
| AZTREONAM | 3 | 21 | 9.15E−86 |
| LEVOFLOXACIN | 5 | 25 | 1.58E−76 |
| PIPERACILLIN | 3 | 25 | 3.63E−72 |
| DEFERIPRONE | 3 | 27 | 7.08E−67 |
| IMIPENEM | 3 | 27 | 7.08E−67 |
| TIGECYCLINE | 3 | 27 | 7.08E−67 |

In this example, an explanation is provided for a predicted connection between the potential drug target IL6R and the adverse event neutropenia. In this case, the matrix includes adverse events (AEs) and conditions on one side and genes/drugs/cell types on the other. The total number of AEs/conditions is N=9097 and the number of AEs/conditions for IL6R is n=10. For the most similar gene, FCN1, the number of associated AEs/conditions is R=13, and the number of shared AEs/conditions with IL6R is 3. This yields a chi-squared probability of ChiSquared (9097, 10, 13, 3)=5.04× 10$^{-138}$. This finding provides possible new insight into the mechanisms by which IL6R targeted therapies may cause certain side effects in patients.

Figure 3:
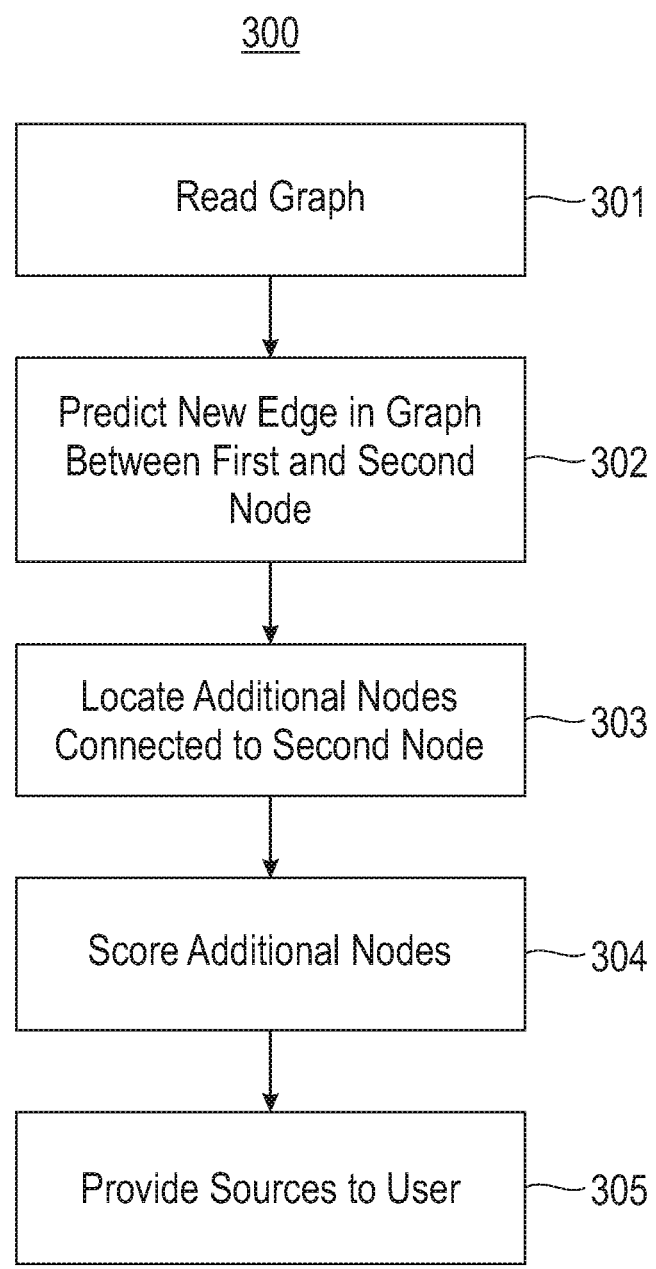
FIG. 3 illustrates a method of providing context for predicted biologic connections according to embodiments of the present disclosure.

Referring now to FIG. 3, a method of providing context for predicted biologic connections is illustrated according to embodiments of the present disclosure. At 301 a graph is read. The graph comprises a plurality of nodes. Each of the plurality of nodes corresponds to an entity or property. The plurality of nodes is interconnected by a plurality of edges. Each edge corresponds to a relationship between connected nodes. At 302, a new edge in the graph is predicted. The new edge corresponds to a relationship between a first node and a second node. The first node corresponds to an entity and the second node corresponds to an entity or property. At 303, one or more additional nodes connected to the second node is located. At 304, the one or more additional nodes is scored according to its connections in common with the first node. At 305, one or more sources is provided to a user describing the connection between the one or more additional node and the second node.

Accordingly, various embodiments provide the rationale behind predicted connections between entities by identifying analogous entities and connections. All domain relevant entity relationships are extracted from relevant scientific literature. This connected graph is represented as a binary matrix. The matrix is factorized to make a prediction. It will be appreciated that additional methods for making such a predication may be used according to the present disclosure. For the prediction, similar rows/columns in the matrix are found that have the predicted value. Each related row/column is scored using a probability calculation. The user is presented with a list or related examples and the evidence for the connection to the predicted element. Sentences from the text source are provided for context.

Figure 4:
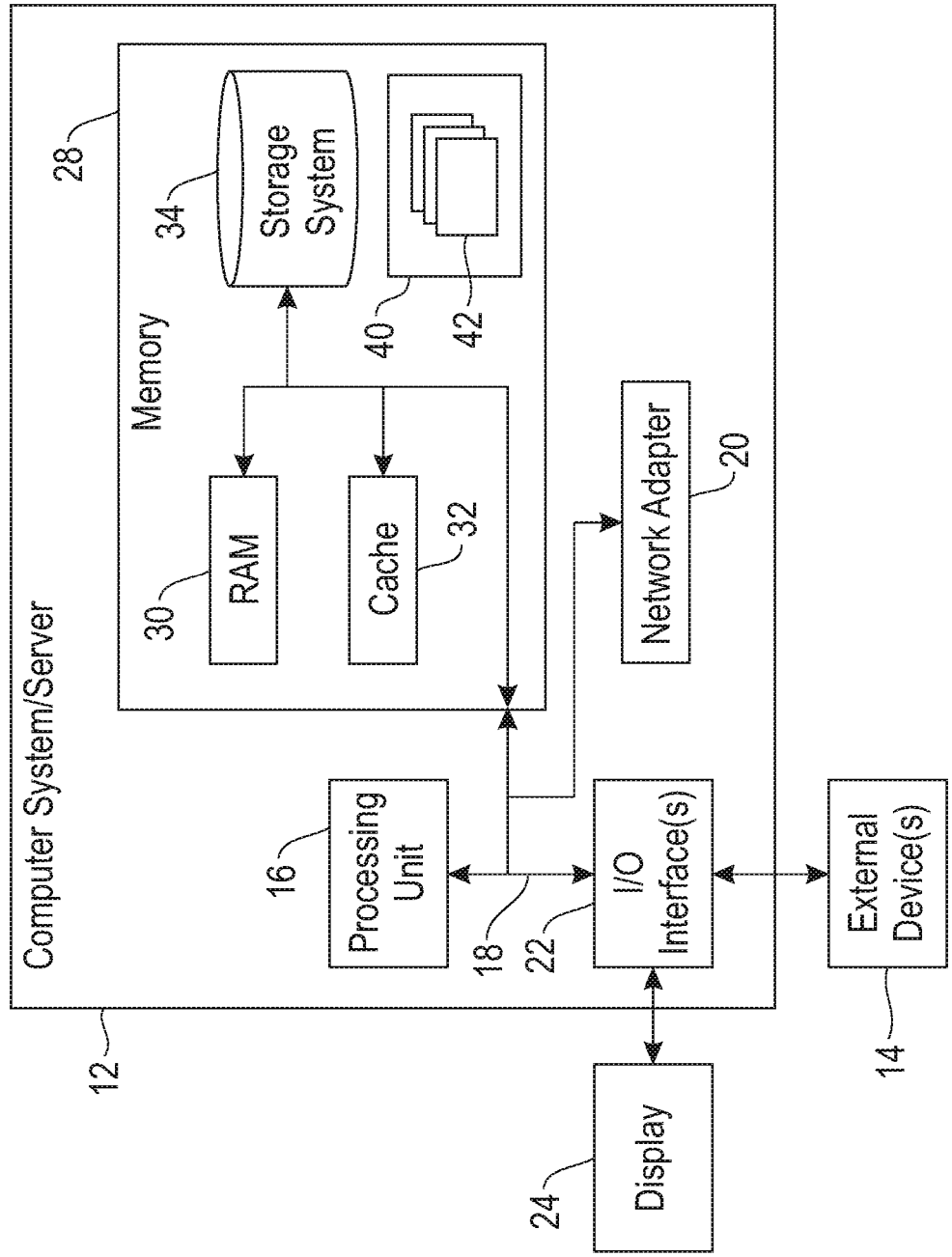
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    reading a graph comprising a plurality of nodes, each of the plurality of nodes corresponding to an entity or property, the plurality of nodes being interconnected by a plurality of edges, each edge corresponding to a relationship between connected nodes;
    predicting a new edge in the graph, the new edge corresponding to a predicted relationship between a first node and a second node, the first node corresponding to an entity and the second node corresponding to an entity or property;
    locating one or more additional nodes connected to the second node, thereby determining a set of relationships including the second node's corresponding entity or property;
    ordering the set of relationships according to their similarity to the predicted relationship;
    providing to a user one or more sources associated with those of the set of relationships having the highest order.

2. The method of claim 1, wherein the entities comprise a gene, a target, a disease condition, or a phenotype.

3. The method of claim 1, wherein the relationships comprise acts-on or has-property.

4. The method of claim 1, wherein the graph is represented as a matrix.

5. The method of claim 2, wherein the matrix is a binary matrix.

6. The method of claim 1, further comprising:
    providing to the user one or more extracts of the one or more sources, the extracts describing the connection between the one or more additional node and the second node.

7. The method of claim 1, further comprising:
    constructing the graph by textual analysis of existing literature.

8. The method of claim 1, wherein ordering the set of relationships comprises:
    computing a probability of random occurance.

9. The method of claim 8, wherein computing the probability comprises computing a chi squared probability.

10. The method of claim 8, wherein computing the probability comprises applying Fisher's exact test.

11. The method of claim 4, wherein predicting the new edge in the graph comprises:
    factorizing the matrix and computing a product matrix therefrom.

12. The method of claim 11, wherein scoring the one or more additional nodes comprises:
    locating non-zero values in the product matrix.

13. The method of claim 10, wherein factorizing the matrix comprises applying alternating least squares matrix factorization.

14. A system comprising:
    a computing node comprising a computer readable storage medium having program instructions embodied therewith, the program instructions executable by a processor of the computing node to cause the processor to perform a method comprising:
        reading a graph comprising a plurality of nodes, each of the plurality of nodes corresponding to an entity or property, the plurality of nodes being interconnected by a plurality of edges, each edge corresponding to a relationship between connected nodes;
        predicting a new edge in the graph, the new edge corresponding to a predicted relationship between a first node and a second node, the first node corresponding to an entity and the second node corresponding to an entity or property;
        locating one or more additional nodes connected to the second node, thereby determining a set of relationships including the second node's corresponding entity or property;
        ordering the set of relationships according to their similarity to the predicted relationship;
        providing to a user one or more sources associated with those of the set of relationships having the highest order.

15. A computer program product for providing context for predicted biologic connections, the computer program product comprising a non-transitory computer readable storage medium having program instructions embodied therewith, the program instructions executable by a processor to cause the processor to perform a method comprising:
    reading a graph comprising a plurality of nodes, each of the plurality of nodes corresponding to an entity or property, the plurality of nodes being interconnected by a plurality of edges, each edge corresponding to a relationship between connected nodes;
    predicting a new edge in the graph, the new edge corresponding to a predicted relationship between a first node and a second node, the first node corresponding to an entity and the second node corresponding to an entity or property;
    locating one or more additional nodes connected to the second node, thereby determining a set of relationships including the second node's corresponding entity or property;
    ordering the set of relationships according to their similarity to the predicted relationship;
    providing to a user one or more sources associated with those of the set of relationships having the highest order.

* * * * *